(12) United States Patent
Hsieh et al.

(10) Patent No.: US 6,687,329 B1
(45) Date of Patent: Feb. 3, 2004

(54) COMPUTER AIDED ACQUISITION OF MEDICAL IMAGES

(75) Inventors: Jiang Hsieh, Brookfield, WI (US); Gopal B. Avinash, New Berlin, WI (US); Cherik Bulkes, Sussex, WI (US); John M. Sabol, Sussex, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/439,103

(22) Filed: May 15, 2003

Related U.S. Application Data

(63) Continuation of application No. 10/242,975, filed on Sep. 13, 2002, now Pat. No. 6,574,304.

(51) Int. Cl.$^7$ ................................................. A61B 6/00
(52) U.S. Cl. .............................. 378/62; 378/8; 378/94; 382/131
(58) Field of Search .......................... 378/4, 8, 19, 62, 378/901; 382/128, 131

(56) References Cited

U.S. PATENT DOCUMENTS 6,434,262 B2 * 8/2002 Wang .......................... 382/132
6,574,304 B1 * 6/2003 Hsieh et al. ................... 378/62

* cited by examiner

Primary Examiner—David V. Bruce
(74) Attorney, Agent, or Firm—Fletcher Yoder

(57) ABSTRACT

The invention provides a technique for acquiring subsequent image data in a medical diagnostic context based upon analysis of initial image data. The initial image data is processed via a computer aided diagnosis algorithm to determine whether additional image data acquisition is appropriate. Subsequent acquisition processes may be performed on the same imaging system from which the initial image data originated, or a different imaging system. The imaging systems may also be of different modalities. The subsequent acquisition of image data may be performed automatically without operator intervention, or the prescribed subsequent acquisition sequence may be outputted by the system for execution upon command of an operator.

24 Claims, 7 Drawing Sheets

COMPUTER AIDED ACQUISITION OF MEDICAL IMAGES

This is a continuation of Ser. No. 10/242,975 filed Sep. 13, 2002 now U.S. Pat. No. 6,574,304.

BACKGROUND OF THE INVENTION

The present invention relates generally to imaging procedures. Particularly, the present invention relates to a method for improving computer aided detection or diagnosis by utilizing a computer aided processing technique.

Computer aided diagnosis (CAD), such as screening mammography and evaluation of other disease states or medical or physiological events, is typically based upon various types of analysis of a series of collected images. The collected images are analyzed by utilizing the pathologies that are highlighted by a CAD algorithm. The results are generally viewed by radiologists for final diagnosis. As can be appreciated by those skilled in the art, certain subsequent imaging procedures may become feasible or may be recognized as desirable due to the improved management of data volume.

It should be noted that computer aided CAD may be utilized in any imaging modality, such as computed tomography (CT), magnetic resonance imaging (MRI), X-ray systems, ultrasound systems, positron emission tomography (PET), and so forth. CAD algorithms in certain of these modalities may provide advantages over those in other modalities, depending upon the imaging capabilities of the modality, the tissue being imaged, and so forth. Computed tomography, for example, is generally a diagnostic procedure in which cross-sectional images or slices are made by an X-ray system. The CT scanning procedure combines the use of a computer system and a rotating X-ray device to create detailed cross sectional images or "slices" of a patient's organs and other body parts. The imaging capabilities are physically similar to those of X-ray systems. MRI, ultrasound, PET, and other modalities similarly are adapted to imaging certain tissues or anatomies, and provide advantages for the different CAD algorithm employed with images they produce.

Each imaging modality is based upon unique physics and image processing techniques. For example, a CT system measures the attenuation of X-ray beams passed through a patient from numerous angles, and then, based upon these measurements, a computer is able to reconstruct images of the portions of a patient's body responsible for the radiation attenuation. As will be appreciated by those skilled in the art, these images are based upon separate examination of a series of continuous cross sections. Thus, a virtual 3-D image may be produced by a CT examination. It should be pointed out that a CT system does not actually directly provide an image, but rather numerical values of tissue density. The image based upon the reconstructed data is typically displayed on a cathode ray tube, and may be printed or reproduced on film.

Continuing with the example of CT imaging, CT scanners operate by projecting fan shaped X-ray beams from an X-ray source that is collimated and passes through the object, such as a patient, that is then detected by a detector element. The data is then used to produce a useful image. Thus, the detector element produces data based on the attenuation of the X-ray beams, and the data are processed by computer analysis. The locations of pathologies may then be highlighted by the CAD algorithm, and thus brought to a human observer's attention. The results may then be reviewed by a radiologist or other physician for final diagnosis.

Each imaging modality may provide unique advantages over other modalities for certain types of disease or physiological condition detection. For example, CT scanning provides advantages over other types of techniques in diagnosing disease particularly because it illustrates the shape and exact location of organs, soft tissues, and bones any slice of the body. Further, CT scans may help doctors distinguish between a simple cyst, for example, and a solid tumor, and thus evaluate abnormalities more accurately. As mentioned above, other imaging modalities are similarly best suited to imaging other physiological features of interest, and to corresponding CAD algorithms.

Existing techniques for computerized diagnosis of physiological features suffer from certain serious drawbacks. For example, the output of the CAD analysis is generally fairly interactive, requiring assessment and evaluation by a seasoned practitioner. Due to time constraints and the availability of such persons, a patient is often called upon to report for certain types of examination, with further examinations needing to be scheduled, when appropriate, based upon the review of the CAD analysis. That is to say, patients often must return for additional tests on the same or a different modality imaging system in order to properly evaluate and diagnose potential conditions. The resulting procedure is not only time-consuming for the patient and for the physician, but ultimately results in the entire process extending over a considerable period of time. Additional appointments for subsequent imaging can also result in considerable expense both for the patient, for hospitals and clinics, and for insurance carriers.

There is a need, therefore, for improved technique for guiding subsequent image data acquisition based upon analysis by a CAD algorithm. There is a particular need for a technique which would allow additional data to be prescribed and acquired both from the same or from the same type of imaging system as used in initial evaluations, and from other modality systems, where appropriate.

BRIEF DESCRIPTION OF THE INVENTION

The present technique provides an improved method for useful medical images for diagnosing patients that responds to such needs. The technique makes use of initial CAD information to guide additional data acquisition with or without additional human operator assistance. Thus, once a feature of interest is identified by the CAD algorithm a computer may automatically direct the imaging system to re-acquire additional images at the suspected location, or may instruct or suggest that an operator do so.

In accordance with one aspect of the invention, a method is provided for processing an image generated by an imaging system. The method includes acquiring a first series of images from a first imaging system. The first series of images is then processed in accordance with a CAD algorithm. A second series of images is then acquired based upon the results of the CAD algorithm.

In accordance with another aspect of the invention, an imaging system includes a first image data acquisition system configured to acquire medical images, and a computer system. The computer system is coupled to the image data acquisition system and is configured to generate a first series of images from image data acquired by the acquisition system. The computer system is further configured to process the first series of images via a CAD algorithm. The computer system is configured, as well, to prescribe acquisition of a second series of images based upon results of the CAD algorithm.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
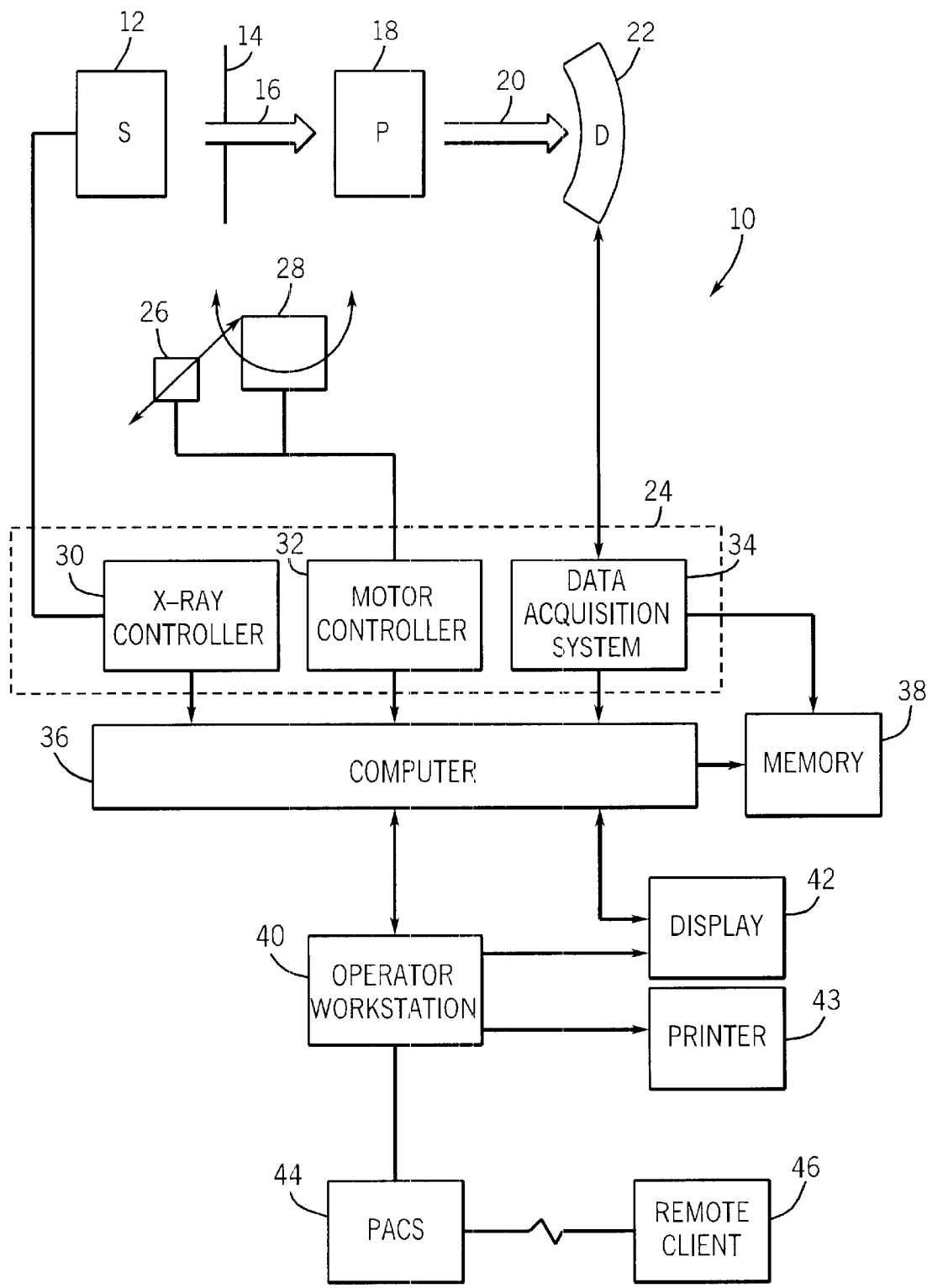
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

Source 12 is controlled by a system controller 24 which furnishes both power and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a rotational subsystem 26 and linear positioning subsystem 28. The rotational subsystem 26 enables the X-ray source 12, collimator 14 and the detector 22 to be rotated around the patient 18. It should be noted that the rotational subsystem 26 may include a gantry. Thus, the system controller 24 may be utilized to operate the gantry. The linear positioning subsystem 28 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 26 and the linear positioning subsystem 28.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and coverts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory to store a large amount of data may be utilized by such an exemplary system 10. Also the computer 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image and to control imaging. Additionally, the scanned image may also be printed on to a printer 43 which may be coupled to the computer 36 and the operator workstation 40. Further, the operator workstation 40 may also be coupled to a picture archiving and communications system (PACS) 44. It should be noted that PACS 44 may be coupled to a remote system 46, radiology department information system (RIS), hospital information system (HIS) or to an internal or external network, so that others at different locations may gain access to the image and to the image data.

It should be further noted that the computer 36 and operator workstation 46 may be coupled to other output devices which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
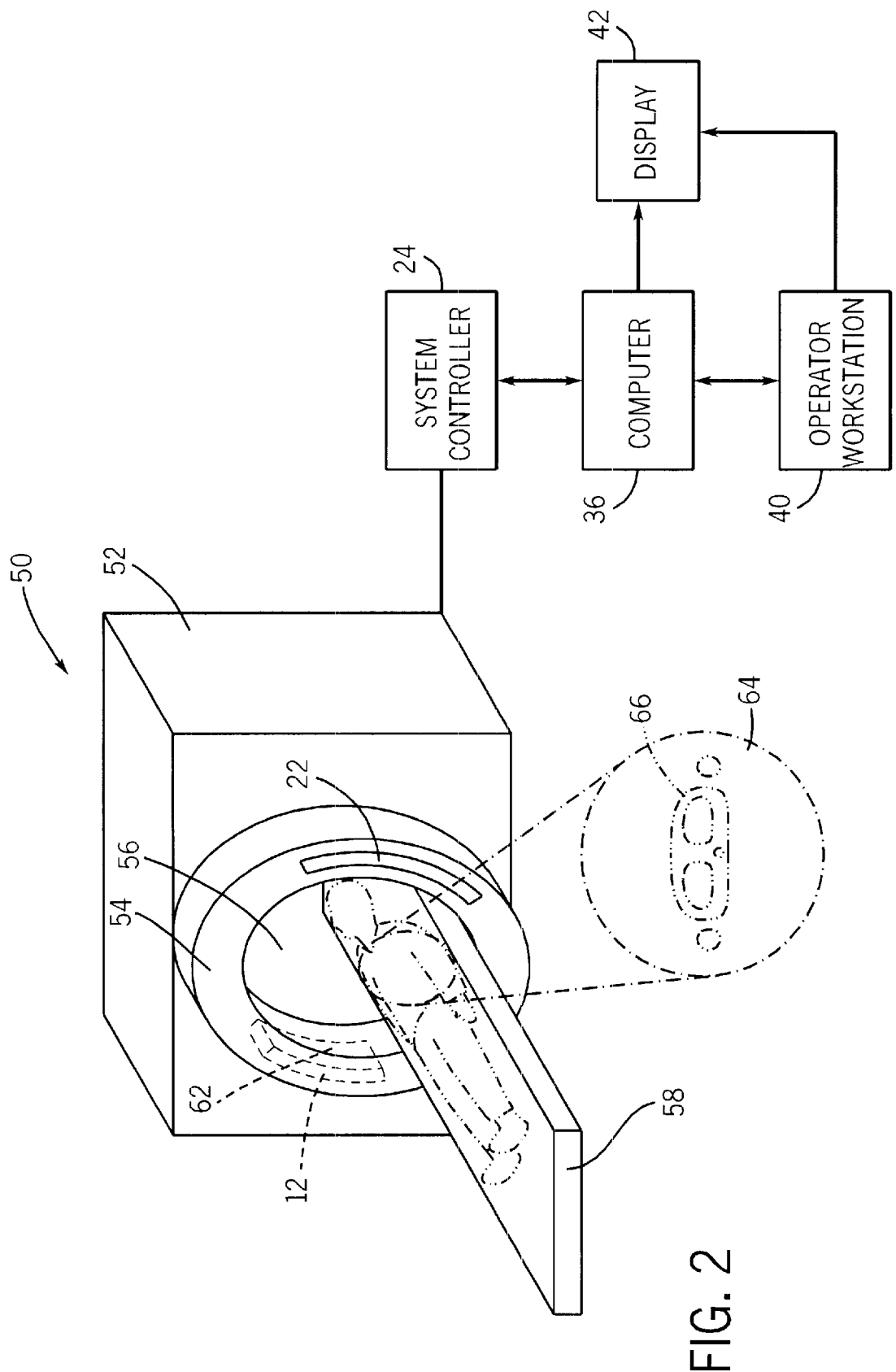
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is illustrated with a frame 52 and a gantry 54 that has an aperture 56. The aperture 56 may typically be 60 cm to 70 cm in diameter. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 28 (see FIG. 1). The gantry 54 is illustrated with the source of radiation 12, typically an X-ray tube which emits X-ray radiation from a focal point 62. The stream of radiation is directed towards a particular region of the patient 18. It should be noted that the particular region of the patient 18 is typically chosen by an operator so that the most useful scan of a region may be imaged.

In typical operation, X-ray source 12 projects an X-ray beam from the focal point 62 and toward detector array 22. The detector 22 is generally formed by a plurality of detector elements which sense the X-rays that pass through and around a subject of interest, such as particular body parts, for instance the liver, pancreas and so on. Each detector element produces an electrical signal that represents the intensity of the X-ray beam at the position of the element at the time the beam strikes the detector. Furthermore, the gantry 54 is rotated around the subject of interest so that a plurality of radiographic views may be collected by the computer 36. Thus, an image or slice is acquired which may incorporate, in certain modes, less or more than 360 degrees of projection, to formulate an image). The image is collimated to a desired thickness, typically between 0.5 mm and 10 mm using either lead shutters in front of the X-ray source 12 and different detector apertures 22. The collimator 14 (see FIG. 1) typically defines the size and shape of the X-ray beam that emerges from the X-ray source 12.

Thus, as the X-ray source 12 and the detector 22 rotate, the detector 22 collects data of the attenuated X-ray beams. Data collected from the detector 22 then undergo pre-processing and calibration to condition the data to represent the line integrals of the attenuation coefficients of the scanned objects. The processed data, commonly called projections, are then filtered and backprojected to formulate an image of the scanned area. As mentioned above, the computer 36 is typically used to control the entire CT system 10. The main computer that controls the operation of the system may be adapted to control features enabled by the system controller 24. Further, the operator workstation 40 is coupled to the computer 36 as well as to a display, so that the reconstructed image may be viewed.

Once reconstructed, the image produced by the system of FIGS. 1 and 2 reveals internal features of a patient. As illustrated generally in FIG. 2, the image 64 may be displayed to show these features, such as indicated at reference numeral 66 in FIG. 2. In traditional approaches to diagnosis of medical conditions, such as disease states, and more generally of medical events, a radiologist or physician would consider a hard copy of display of the image 64 to discern characteristic features of interest. Such features might include lesions, sizes and shapes of particular anatomies or organs, and other features which would be discernable in the image based upon the skill and knowledge of the individual practitioner.

The present technique implements certain of these capabilities by CAD algorithms. As will be appreciated by those skilled in the art, CAD algorithms may offer the potential for identifying, or at least localizing, certain features of interest, such as anatomical anomalies. The particular CAD algorithm is commonly selected based upon the type of feature to be identified, and upon the imaging modality used to create the image data. The CAD technique may employ segmentation algorithms, which identify the features of interest by reference to known or anticipated image characteristics, such as edges, identifiable structures, boundaries, changes or transitions in colors or intensities, changes or transitions in spectrographic information, and so forth. Current CAD algorithms generally offer the potential for identifying these features only. Subsequent processing and data acquisition is, then, entirely at the discretion and based upon the expertise of the practitioner.

CAD algorithms may be considered as including several parts or modules, all of which may be implemented in the present technique. In general, the CAD algorithm may include modules such as accessing image data, segmenting data or images, feature selection or extraction, classification, training, and visualization. Moreover, the CAD processing may be performed on an acquisition projection data set prior to reconstruction, on two-dimensional reconstructed data (both in axial and scout modes), on three-dimensional reconstructed data (volume data or multiplanar reformats), or a suitable combination of such formats. The acquired projection data set may have a number of one-dimensional projections for two-dimensional scans or a number of two-dimensional projections for three-dimensional scans. Using the acquired or reconstructed data, segmentation, feature selection, classification prior to visualization may be performed. These basic processes can be done in parallel, or in various combinations.

The data on which the CAD algorithm is implemented may be raw image acquisition system information, or may be partially or completely processed data. The data may originate from a tomographic data source, or may be diagnostic tomographic data (such as raw data in projection or Radon domain in CT imaging, single or multiple reconstructed two-dimensional images, or three-dimensional reconstructed volumetric image data).

The segmentation portion of the CAD algorithm may identify a particular region of interest based upon calculated features in the tomographic data. The region of interest can be determined in a number of manners, using an entire data set or using part of a data set, such as a candidate mass region in a specific area. The particular segmentation technique may depend upon the anatomies to be identified, and may typically be based upon iterative thresholding, K-means segmentation, edge detection, edge linking, curve fitting, curve smoothing, two- and three-dimensional morphological filtering, region growing, fuzzy clustering, image/volume measurements, heuristics, knowledge-based rules, decision trees, neural networks, and so forth. Alternatively, the segmentation may be at least partially manual. Automated segmentation may also use prior knowledge such as shape and size of a mass to automatically delineate an area of interest.

The feature extraction aspect of the CAD algorithm involves performing computations on the data which comprises the desired images. Multiple feature measures can be extracted from the image-based data using region of interest statistics, such as shape, size, density, and curvature. For projection space data, features such as location, shape, or size of feature projections in a view or location may be used, such as to provide consistency between views.

The classification aspects of the CAD algorithm may be, again, partially or fully manual or automated. In particular, the classification may be used to specifically identify regions of interest, such as by classification as normal or abnormal anatomies or lesions. Bayesian classifiers, neural networks, rule-based methods or fuzzy logic techniques, among others, can be used for classification. It should be noted that more than one CAD algorithm can be employed in parallel. Such parallel operation may involve performing CAD operations individually on portions of the image data, and combining the results of all CAD operations (logically by "and", "or" operations or both). In addition, CAD operations to detect multiple disease states or anatomical features of interest may be performed in series or in parallel.

Prior to classification of masses for anatomies using the CAD algorithm, prior knowledge from training may be incorporated. The training phase may involve the computation of several candidate features on known samples of normal and abnormal lesions or other features of interest. A feature selection algorithm may then be employed to sort through the candidate features and select only the useful ones and remove those that provide no information, or redundant information. This decision is based upon classification results with different combinations of candidate features. The feature selection algorithm may also be used to reduce the dimensionality for practical reasons of processing, storage and data transmission. Thus, optimal discrimination may be performed between features or anatomies identified by the CAD algorithm.

The visualization aspect of the CAD algorithm permits reconstruction of useful images for review by human or machine observers. Thus, various types of images may be presented to the attending physician or to any other person needing such information, based upon any or all of the processing and modules performed by the CAD algorithm. The visualization may include two- or three-dimension renderings, superposition of markers, color or intensity variations, and so forth.

The present technique offers the potential for further enhancing the automation offered by CAD techniques by enabling either further processing image data or further acquisition of image data. In the case of processing, various parameters employed in post-processing of the acquired image data may be altered so as to render the reconstructed image more revealing or useful in identifying, localizing and diagnosing a physiological condition. In particular, such parameters may include contrast, spatial resolution (e.g. zoom), color, and so forth. Moreover, the post-processing based upon the results of initial CAD evaluation may include mathematical evaluations such as segmentation, registration, computation of areas or volumes, and so forth. The "post-processing" may also involve the use of different reconstruction algorithms or different reconstruction parameters to generate images. For example, based on initial CAD results, different filter kernels (Soft, Standard, Detail, Bone, Edge, Lung, etc.) may be used to produce additional images from the original scan. Different filter kernels enhance different desired features in the image. Other reconstruction parameters, such as reconstruction field-of-view, matrix size, targeting locations, etc. can also be modified to produce additional images based on the initial CAD results.

The initial CAD evaluation may also enable the automatic acquisition of subsequent images so as to enable a complete useful set of information to be gathered during a single patient session. The subsequent processing may be in order due, for example, to particular features which appear in images initially acquired but are not adequately shown. Thus, the subsequent acquisition may include acquisition of data from other regions of the patient's body, at different orientations with respect to tissues of interest, at different resolution levels, and so forth. Moreover, entirely different acquired data may be desired based upon the initial CAD evaluation, such as data acquired via an entirely different modality system.

Figure 3:
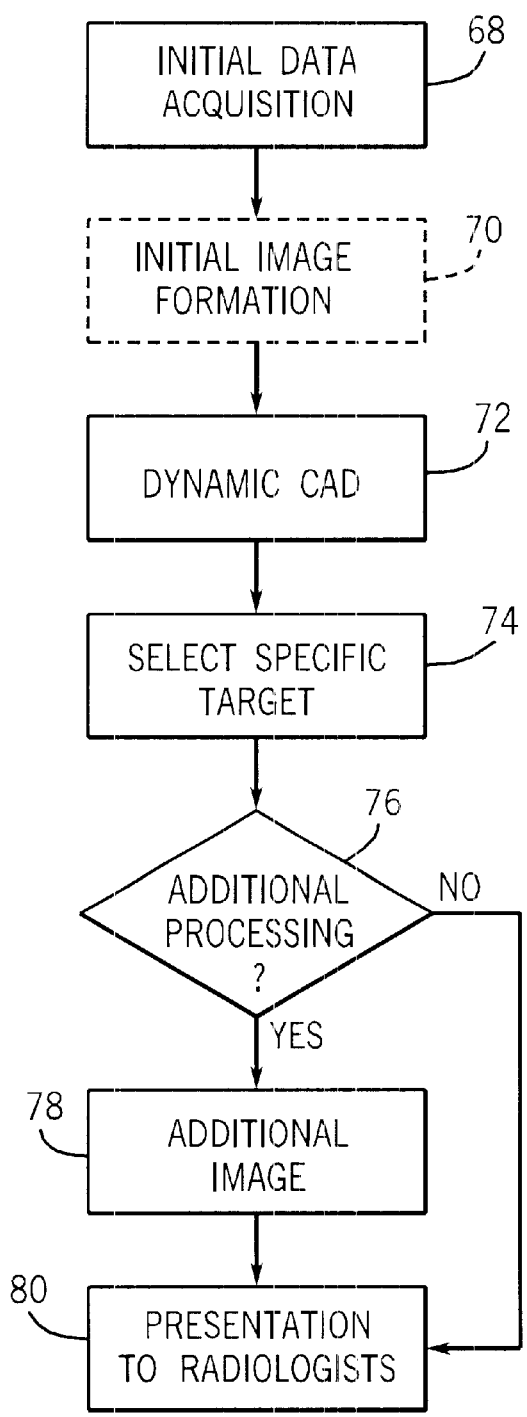
FIG. 3 is a flow chart illustrating exemplary steps in logic for carrying out subsequent image data processing based upon CAD analysis of acquired image data.

FIG. 3 represents a flow chart of exemplary steps in carrying out a processing routine based upon CAD analysis. The technique summarized in FIG. 3 begins at step 68 where initial data acquisition is performed. As noted above, this data acquisition may be based upon any suitable imaging modality, typically selected in accordance with the particular anatomy to the imaged and the analysis to be performed. By way of example, those skilled in the art will recognize that the physical limitation of certain imaging modalities render them more suitable for imaging soft tissues as opposed to bone or other more dense tissue or objects. Moreover, the modality may be coupled with particular settings, also typically dictated by the physics of the system, to provide higher or lower contrast images, volume rendering, sensitivity or insensitivity to specific tissues or components, and so forth. Finally, the image acquisition may be coupled with the use of contrast agents or other markers used to target or highlight particular features or areas of interest. In a CT system, for example, the image data acquisition of step 68 is typically initiated by an operator interfacing with the system via the operator workstation 40 (see FIG. 2). Readout electronics detect signals generated by virtue of the impact radiation on the scanner detector, and the system processes these signals to produce useful image data.

At step 70 of FIG. 3, the initial image is formed. The formation of the image at step 70 may include reconstruction and display of the image, or simply processing of the image data. In general, a reconstructed image may be useful by a physician or operator of the system to guide in the subsequent processing or image data acquisition steps. In other situations, it may be desirable to actually reconstruct and display the image, but the image data is nevertheless analyzed as described below. Step 70 will also typically include storage of the image data for subsequent processing.

At step 72, a CAD algorithm is carried out on the acquired image data. As noted above, the CAD algorithm will typically be selected in accordance with the imaging modality and with the particular data type and anatomy represented in the image. The CAD analysis may identify various features of interest, including disease states, lesions, or any other physiological feature of interest. Based upon the analysis, a target region is selected as summarized in step 74 in FIG. 3. The target region may be larger or smaller than a similar region of the initial image, or may be of a different or adjacent region. By way or example, the target region selected at step 74 may provide for greater spatial resolution (e.g. zoom-in) of a potential lesion. The target region is preferably selected automatically based upon the output of the CAD analysis performed at step 72. Where, for example, the CAD analysis indicates that subsequent processing may reveal additional details in an image, a target region corresponding to the location of such details will be selected at step 74.

Based upon the target selection of step 74 and upon the CAD analysis performed at step 72, additional processing may be in order as summarized at step 76 in FIG. 3. Such additional processing may include enhancement of certain features in the image, contrast of certain features, edge or structure detection, reprocessing of spatial resolutions (e.g. zooming in or zooming out), or any other suitable processing steps that may be performed upon the acquired image data.

The additional processing at step 76 may also include automatic segmentation, calculation of sizes or volumes of features of interest, and so forth. The additional processing at step 76 may also include automatic selection of optimal parameters used in the reconstruction and produce additional images based on the optimal parameters. If such additional processing is desired, the processing is performed and a subsequent or additional image data set may be generated as indicated at step 78. This image data set may be stored separately for display or review. The image data set will differ from the original processed data by the subsequent processing programmed at step 76. Following a generation of the additional image at step 78, or if no additional processing is in order at step 76, the procedure advances to step 80 where some or all of the reconstructed images may be presented to physicians or radiologists.

It should be noted that, as mentioned above, while initial images may be reconstructed and the. CAD algorithm applied to the image data as described herein, the analysis may be partially or fully performed without such initial visualization. Thus, in case of CT image data, some or all of the CAD algorithm analysis may take place in Radon space. Ultimate useful image reconstruction may include visualizations of initial images, enhanced images, or both. The results of the CAD analysis may, where desired, even guide the type of image reconstruction performed, such as from Radon space in the CT imaging example.

Figure 4:
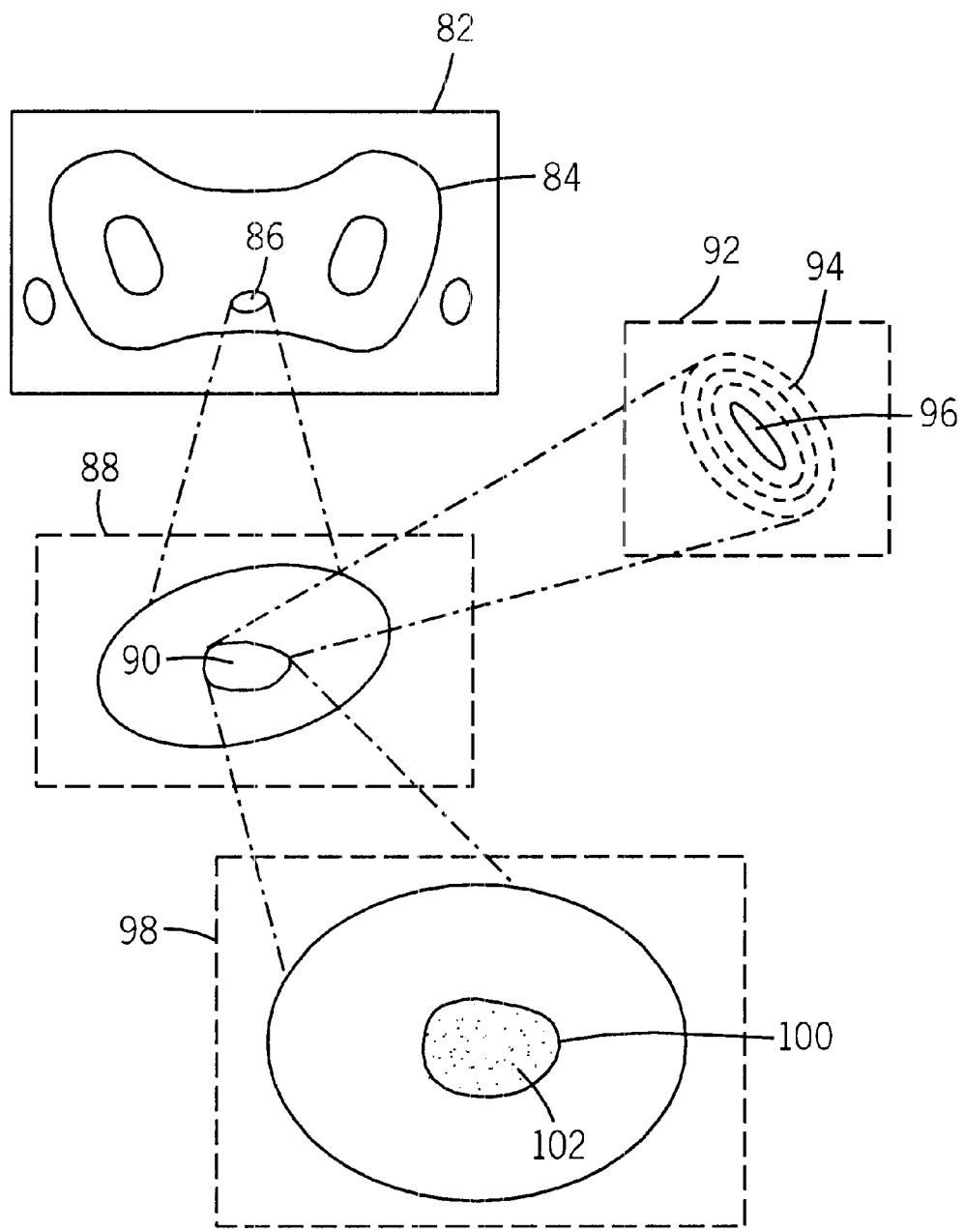
FIG. 4 is a diagrammatical representation of a series of processed images resulting from post-processing based upon CAD analysis.

The foregoing process is summarized diagrammatically in FIG. 4. As shown in FIG. 4, an initial image 82 is acquired that illustrates features 84 potentially of interest. In particular, the features may include specific regions or targets 86 of interest. Subsequent processing, then, may be performed as summarized above to render a subsequent image 88 in which the target 86 is reprocessed, such as for more detailed or analytical rendering. Even within such regions, additional processing may be performed through similar steps to gain additional information on the features of interest. By way of example, in the diagram of FIG. 4, a particular feature 90 is reprocessed, such as through segmentation, to render a subsequent image 92 in which limits 94 of a core object 96 are identified. Additional further processing may be performed, such as indicated at reference numeral 98, to render additional images or image data, such as to further increase spatial resolution of a region 100 containing a feature 102 of interest. It should be noted that the various processing steps based upon sequential CAD analysis may be different from one another. Thus, through the series of images 82, 88, 92 and 98 illustrated in FIG. 4, several different types of post-processing of the image data may be performed. Again, these processes are prescribed as a result of the CAD analysis performed on the acquired image data.

Figure 5:
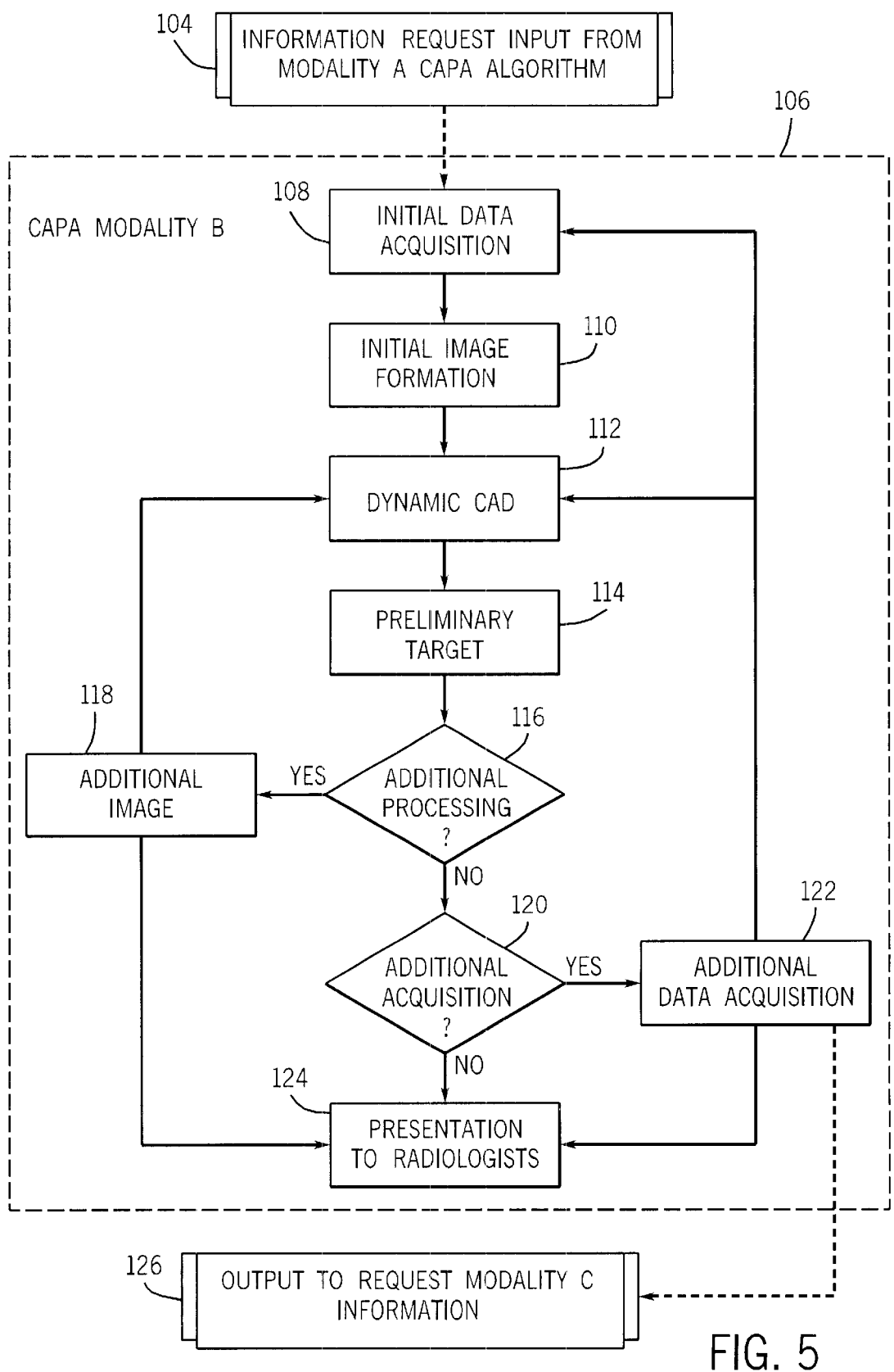
FIG. 5 is a flow chart illustrating exemplary steps in logic for acquiring and processing subsequent image data, including data from different modality imaging systems, based upon results of CAD analysis.

As noted above, the present technique allows for both processing and acquisition of image data based upon CAD analysis. FIG. 5 summarizes exemplary steps in a process in which additional post-processing and/or further data acquisition may be performed. The method of FIG. 5 begin at step 104 where a computer aided processing and acquisition algorithm (CAPA) requests information from a desired imaging modality. In the foregoing example of a CT system, for example, the algorithm may be initiated so as to prescribe a CT scan of a particular anatomy of interest. The CAPA processing, denoted generally by reference numeral 106 then begins. It should be noted that step 104 may include all of the steps summarized above with reference to FIG. 3. That is, an imaging system modality A, such as a CT imaging system, may be used to acquire information, perform initial CAD analysis, reprocess or analyze the image data, and so forth. Where subsequent data acquisition appears to be in order, such as due to the particular anatomy of interest, the imaging capabilities and limitations of the modality system used to acquire the initial information, and so forth, a different modality system may be called into play and employed for the subsequent image data acquisition summarized in FIG. 5. It should also be noted that, as a general matter, FIG. 5 may also be considered to summarize a more general case in which the subsequent image data acquisition sequence is carried out on an imaging system of the same general modality, but with different settings. That is, the process 106 may be performed on the same general type of imaging system, or even the same imaging system, with different settings as determined desirable as a result of the initial CAD analysis.

By way of example, a image data may be acquired from an X-ray system and the image data analyzed to identify a feature of potential interest. Images may be reconstructed based on the X-ray image data. Subsequent image acquisition may then be ordered via a CT system to provide a better view of the particular identified feature. One or more images may then be reconstructed based on the CT image data. As noted above, the actual image reconstruction based on the initial data may be optional, or at least distinct from the analysis performed by the CAD algorithm and the subsequent acquisition of the second image data.

This procedure is illustrated generally in FIG. 5. As summarized in FIG. 5, the subsequent data acquisition begins at step 108 where new initial data is acquired. As noted above, this data acquisition will depend upon the nature of the modality B system, the parameter settings desired to image the features of interest, as well as other parameters dictated by the tissue and the like. At step 110 the image is formed from the acquired data which may be reconstructed for display or simply stored and analyzed. At step 112 a CAD routine is performed on the newly-acquired image data. Again, the CAD routine executed at step 112 will typically be specific to the modality B, its settings, and the features to be imaged or identified. At step 114 a preliminary target is identified, similar to the identification of a target region at step 74 summarized above with reference to FIG. 3. The result from this step may be compared against the initial CAD result to provide complementary information. At step 116 it is determined whether additional processing is desired, and if so, an additional subsequent image data sets are generated based upon such processing as indicated at step 118. The process may continue with further CAD analysis of the subsequent image, as noted above with respect to FIG. 4.

To complete the general case summarized in FIG. 5, following the additional processing, if any, resulting at step 116, even further image data acquisition may be performed as summarized at decision block 120. If such additional data acquisition is in order, this can be performed as indicated at step 122, and the entire process may return to step 108 or step 112 for even further image data acquisition and analysis. If the image data acquisition and analysis on modality B is terminated, images may be reconstructed and presented to attending physicians, clinicians, or radiologist as summarized at step 124. Also in accordance with the more general case of FIG. 5, additional data acquisition prescribed at step 122 may be performed on the same or even further modality systems, such as a modality C as indicated at step 126.

Figure 6:
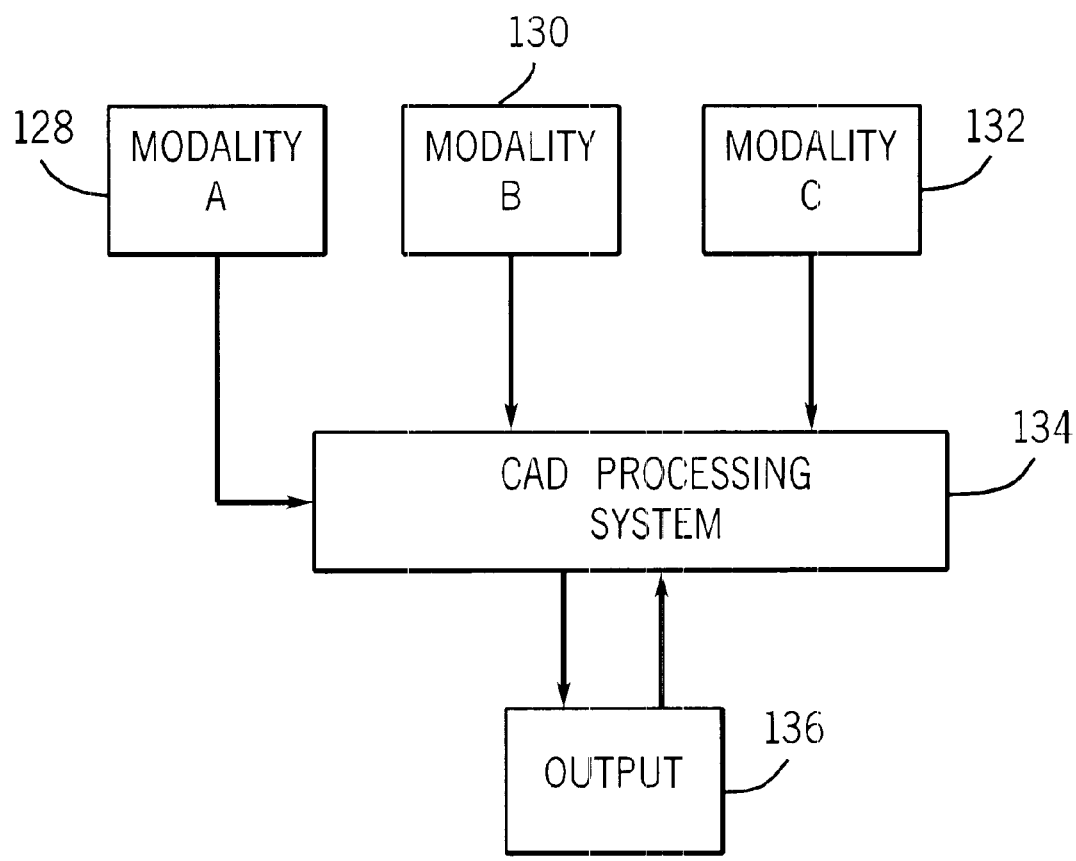
FIG. 6 is a diagrammatical representation of certain functional components of a CAD-based image data acquisition and processing scheme.

The system and inter-system scheme enabled by the processing summarized in FIG. 5 is illustrated diagrammatically in FIG. 6. As shown at FIG. 6, several modality systems 128, 130 and 132 may be used to acquire and process image data. As will be appreciated by those skilled in the art, the modality systems may be similar to one another or may be entirely different and distinct, based upon their own specific physics and imaging principles. Thus, the modalities may include such systems as CT imaging systems, MRI systems, PET systems, ultrasound systems, nuclear medicine systems, and so forth. Input from a first modality is then used as a basis for CAD analysis in a CAD processing system represented generally at reference numeral 134 in FIG. 6. The CAD processing system may be an integral part of the modality imaging system, or may be separate and distinct, even remote from the imaging system. Based upon the CAD analysis performed by this system, subsequent processing may be performed on the same image data set, or additional image data may be acquired from the same modality or from other modality systems which are more suited to imaging or analysis of the features of interest. Results of the CAD analysis and imaging sequences may be displayed or summarized via various output devices 136, such as screen displays, printers, photographic reproduction equipment, and so forth.

Figure 7:
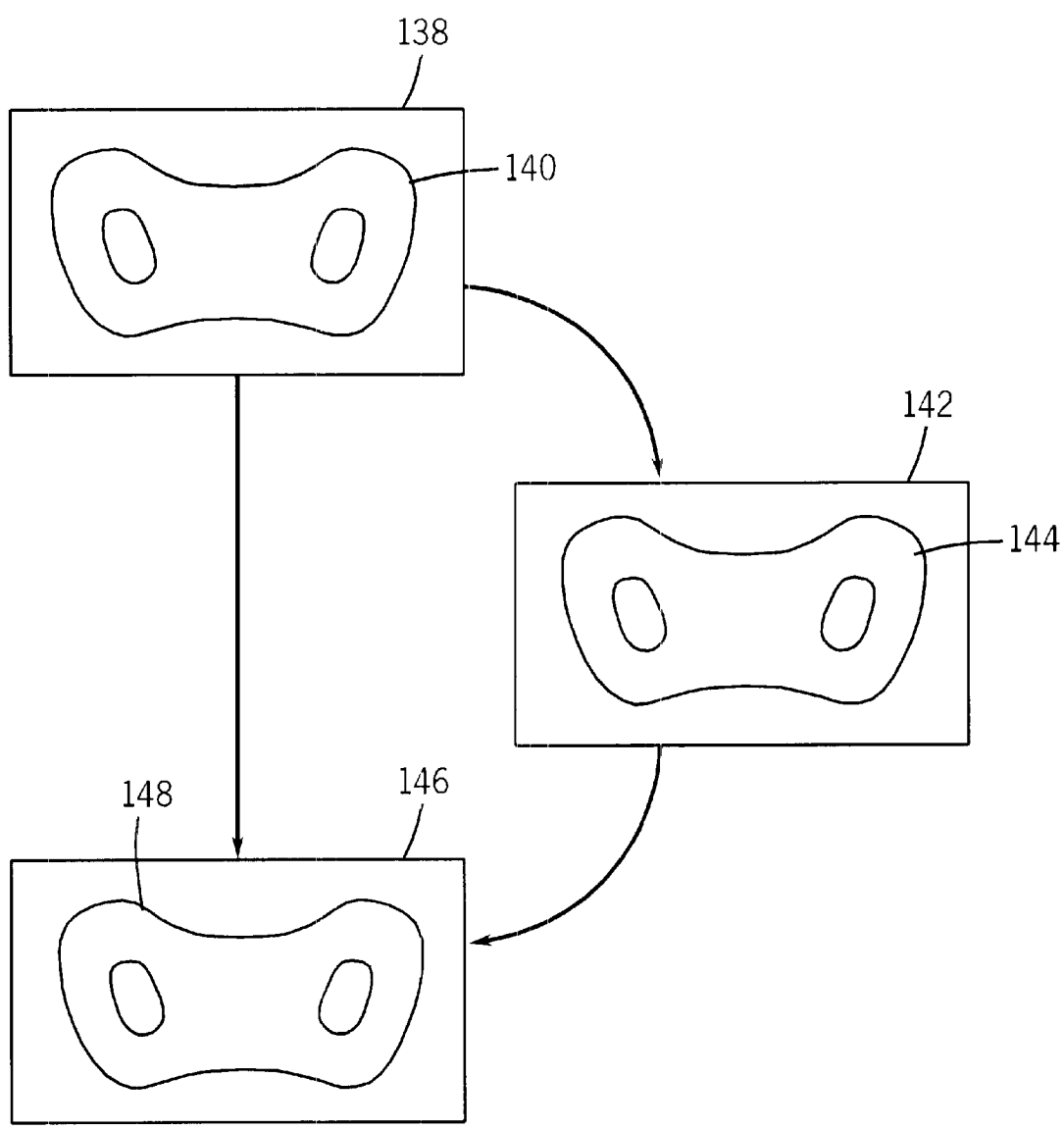
FIG. 7 is a diagrammatical representation of a series of processed images acquired in succession based upon results of CAD analysis of initial image data.

This overall system structure enables a great variety of image acquisition, processing and analysis techniques to be implemented as summarized generally in FIG. 7. In the representation of FIG. 7, an initial image 138 is acquired and analyzed including features of interest 140. Where the image, however, would complimented by image data acquired through different system settings or through a different modality system, subsequent images 142 and 146 may be acquired and analyzed to show the features of interest 144 and 148, either presented in a similar manner or in an entirely different manner, depending upon the processing, image acquisition, and analysis and display desired.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for processing image data comprising:
   (a) accessing at least first image data;
   (b) processing the first image data in accordance with a CAD algorithm, the CAD algorithm performing at least one of segmenting, identifying and classifying a feature of interest in the first image data; and
   (c) prescribing acquisition of at least second image data based upon results of the CAD algorithm.

2. The method of claim 1, wherein the first image data is acquired from a first imaging system, the second image data is prescribed to be acquired from a second imaging system different from the first imaging system.

3. The method of claim 2, wherein the first and second imaging systems are of different imaging modalities.

4. The method of claim 2, wherein at least one of the first and second imaging systems is a CT system.

5. The method of claim 1, wherein the second image data is prescribed to be acquired with a different system configuration than that used for acquiring the first image data.

6. The method of claim 1, further comprising displaying a prescription for acquisition of the second image data.

7. A method for processing image data comprising:
   (a) acquiring first image data via an imaging system;
   (b) processing the first image data in accordance with a CAD algorithm, the CAD algorithm performing at least one of segmenting, identifying and classifying a feature of interest in the first image data; and
   (c) prescribing acquisition of at least second image data based upon results of the CAD algorithm.

8. The method of claim 7, wherein the first image data is acquired from a first imaging system, the second image data is prescribed to be acquired from a second imaging system different from the first imaging system.

9. The method of claim 8, wherein the first and second imaging systems are of different imaging modalities.

10. The method of claim 8, wherein at least one of the first and second imaging systems is a CT system.

11. The method of claim 7, wherein the second image data is prescribed to be acquired with a different system configuration than that used for acquiring the first image data.

12. An imaging system comprising:
    a memory device for storing first image data; and
    a computer system coupled to the memory device and configured to process the first image data in accordance with a CAD algorithm, the CAD algorithm performing at least one of segmenting, identifying and classifying a feature of interest in the first image data; and to prescribe acquisition of at least second image data based upon results of the CAD algorithm.

13. The imaging system of claim 12, further comprising an image data acquisition system configured to acquire first image data.

14. The imaging system of claim 13, further comprising a second image data acquisition system, wherein the second image data is prescribed to be acquired from the second image data acquisition system.

15. The imaging system of claim 12, wherein the second image data is prescribed to be acquired with a different system configuration than that used for acquiring the first image data.

16. The method of claim 12, further comprising a display for displaying a prescription for acquisition of the second image data.

17. A system for generating images comprising:
    an X-ray source;
    a detector configured to receive radiation from the X-ray source and to generate image data based thereon;
    a computer system coupled to the detector and configured to analyze the image data in accordance with a CAD algorithm, the CAD algorithm performing at least one of segmenting, identifying and classifying a feature of interest in the first image data, and to prescribe acquisition of additional image data based upon results of the CAD algorithm.

18. The system of claim 17, wherein the additional image data is prescribed to be acquired from the detector.

19. The system of claim 17, further comprising a second image data acquisition system, wherein the additional image data prescribed to be acquired from the second image data acquisition system.

20. The system of claim 17, wherein X-ray source and detector are part of a CT imaging system.

21. An imaging system comprising:
    means for accessing at least first image data;
    means for processing the first image data in accordance with a CAD algorithm, the CAD algorithm performing at least one of segmenting, identifying and classifying a feature of interest in the first image data; and means for prescribing acquisition of at least second image data based upon results of the CAD algorithm.

22. An imaging system comprising:

mean for acquiring first image data via an imaging system;

means for processing the first image data in accordance with a CAD algorithm, the CAD algorithm performing at least one of segmenting, identifying and classifying a feature of interest in the first image data; and means for prescribing acquisition of at least second image data based upon results of the CAD algorithm.

23. A computer program for processing image data, the program comprising:

at least one machine readable medium; and a computer program stored on the medium and including routines for accessing at least first image data, processing the first image data in accordance with a CAD algorithm, the CAD algorithm performing at least one of segmenting, identifying and classifying a feature of interest in the first image data, and prescribing acquisition of at least second image data based upon results of the CAD algorithm.

24. A computer program for processing image data, the program comprising:

at least one machine readable medium; and a computer program stored on the medium and including routines for acquiring first image data via an imaging system, processing the first image data in accordance with a CAD algorithm, the CAD algorithm performing at least one of segmenting, identifying and classifying a feature of interest in the first image data, and prescribing acquisition of at least second image data based upon results of the CAD algorithm.

* * * * *